(12) United States Patent
Nakayama et al.

(10) Patent No.: US 10,018,578 B2
(45) Date of Patent: Jul. 10, 2018

(54) X-RAY ANALYSIS DEVICE

(71) Applicant: Hitachi High-Tech Science Corporation, Tokyo (JP)

(72) Inventors: Satoshi Nakayama, Tokyo (JP); Keiichi Tanaka, Tokyo (JP); Atsushi Nagata, Tokyo (JP); Kazuo Chinone, Tokyo (JP)

(73) Assignee: Hitachi High-Tech Science Corporation, Tokyo (JP)

( * ) Notice: Subject to any disclaimer, the term of this patent is extended or adjusted under 35 U.S.C. 154(b) by 181 days.

(21) Appl. No.: 15/246,041

(22) Filed: Aug. 24, 2016

(65) Prior Publication Data
US 2017/0062088 A1 Mar. 2, 2017

(30) Foreign Application Priority Data

Aug. 26, 2015 (JP) .................................. 2015-166549

(51) Int. Cl.
*G01N 23/20* (2018.01)
*G01N 23/223* (2006.01)

(52) U.S. Cl.
CPC .................................. *G01N 23/223* (2013.01)

(58) Field of Classification Search
None
See application file for complete search history.

(56) References Cited

U.S. PATENT DOCUMENTS

| | | | |
|---|---|---|---|
| 9,619,730 B2* | 4/2017 | Pavlovich | A61B 6/032 |
| 2011/0064191 A1* | 3/2011 | Toth | G01N 23/20033 378/53 |
| 2015/0177167 A1* | 6/2015 | Tanaka | G01N 23/20091 378/49 |
| 2015/0223766 A1* | 8/2015 | Besson | G01T 1/2985 378/5 |

FOREIGN PATENT DOCUMENTS

JP 2002071591 A 3/2002

OTHER PUBLICATIONS

D.A. Wollman et al., "High-resolution, energy-dispersive microcalorimeter spectrometer for X-ray microanalysis," Journal of Microscopy, vol. 188, Pt 3, Dec. 1997, pp. 196-223.

* cited by examiner

*Primary Examiner* — Hoon Song
(74) *Attorney, Agent, or Firm* — Wood Herron & Evans LLP

(57) ABSTRACT

An X-ray analysis device includes an electron gun, an X-ray optical member, a first detection unit and a second detection unit, and a distance changing mechanism. The X-ray optical member guides characteristic X-rays emitted from a sample to at least any one of the first detection unit or the second detection unit. The first detection unit is formed such that energy resolution is given relative priority over counting efficiency in contrast to the second detection unit. The second detection unit is formed such that counting efficiency is given relative priority over energy resolution in contrast to the first detection unit. The distance changing mechanism (Continued)

changes the distance between each of the first detection unit and the second detection unit and the X-ray optical member in an axial direction of an optical axis of the X-ray optical member.

6 Claims, 11 Drawing Sheets

(FIRST STATE)

(SECOND STATE)

X-RAY ANALYSIS DEVICE

BACKGROUND OF THE INVENTION

Field of the Invention

The present invention relates to an X-ray analysis device including an energy dispersive radiation detector, such as a superconducting transition edge sensor. The present application claims priority based on Japanese Patent Application No. 2015-166549 filed in Japan on Aug. 26, 2015, the disclosures of which are incorporated herein by reference in their entirety.

Description of Related Art

As an X-ray analysis device which can perform energy discrimination of X-rays, an energy dispersive X-ray detector (Energy Dispersive Spectroscopy, hereinafter, referred to as EDS) or a wavelength dispersive X-ray detector (Wavelength Dispersive Spectroscopy, hereinafter, referred to as WDS) is known.

An EDS is a type of X-ray detector which converts the energy of X-rays taken into the detector to an electrical signal in the detector and calculates energy according to the magnitude of the electrical signal. A WDS is a type of X-ray detector which monochromatizes (energy discrimination) X-rays using a spectroscope and detects the monochromatized X-rays using a proportional counter or the like.

As an EDS, a semiconductor detector, such as a SiLi (silicon lithium) type detector, a silicon drift type detector, or a germanium detector, is known. For example, a silicon lithium type or silicon drift type detector is frequently used in an element analysis device, such as an electron microscope, and can detect a wide range of energy of about 0.2 keV to 20 keV. However, since silicon is used in the detector, in principle, the properties of the detector depend on the bandgap (about 1.1 eV) of silicon, it is difficult to improve energy resolution to about 130 eV or more, and energy resolution is degraded by 10 times or more compared to a WDS.

In this way, when the energy resolution which is one index indicating the performance of an X-ray detector is, for example, 130 eV, this means that, if the X-ray detector is irradiated with X-rays, energy can be detected with uncertainty of about 130 eV. Accordingly, the smaller the uncertainty, the higher the energy resolution. That is, in a case of detecting characteristic X-rays having two adjacent spectrums, if the energy resolution becomes higher, the uncertainty becomes smaller. If the energy difference between two adjacent peaks is about 20 eV, the two peaks can be separated with energy resolution of about 20 eV to 30 eV in principle.

In recent years, superconducting X-ray detectors which are of the energy dispersive type and have energy resolution equivalent to a WDS have been attracting attention. Of superconducting X-ray detectors, a detector which has a superconducting transition edge sensor (Transition Edge Sensor, hereinafter, referred to as TES) is a high-sensitivity calorimeter using rapid change in resistance during superconduction-normal conduction transition of a metal thin film (for example, when change in temperature is several mK, change in resistance is 0.1Ω, or the like). A TES is also referred to as a microcalorimeter. Of the superconducting X-ray detectors, a superconducting tunnel junction (hereinafter, referred to as STJ) detector detects multiple electric charge carriers tunneling through an insulating layer of a Josephson element as signals. Of the superconducting X-ray detectors, a superconducting strip detector (for example, a Superconducting Single-Photon Detector, hereinafter, referred to as SSPD, or a Superconducting Strip-Line Detector, hereinafter, referred to as SSLD, or the like) is a detector using a fast relaxation process. Of the superconducting X-ray detectors, a microwave kinetic inductance detector (hereinafter, referred to as MKID) detects change in inductance.

The TES detects change in temperature in the TES occurring when fluorescent X-rays or characteristic X-rays generated from a sample due to irradiation of radiation, such as primary X-rays or primary electron beams, are incident, to analyze the sample. A TES has energy resolution higher than those of other detectors, and can obtain energy resolution of 10 eV or less, for example, with characteristic X-rays of 5.9 keV.

In a case where the TES is attached to a scanning electron microscope, a transmission electron microscope, or the like, characteristic X-rays which are generated from a sample irradiated with electron beams are acquired by the TES, whereby it is possible to easily separate a peak of an energy spectrum of characteristic X-rays (for example, Si-K$\alpha$, W-M$\alpha$, W-M$\beta$, and the like) which cannot be separated in a semiconductor type X-ray detector.

The counting efficiency of an X-ray detector is one index indicating the performance of the X-ray detector along with the energy resolution of the X-ray detector. The counting efficiency is an index which changes according to the area, thickness, and material of a radiation receiving portion of the X-ray detector, the distance between a radiation generation source and the X-ray detector, a maximum count rate of the X-ray detector, and the like. For example, the area of a radiation receiving portion of a general silicon drift type detector is several $mm^2$ to hundreds of $mm^2$, and the maximum count rate of a silicon drift type detector is tens of thousands of cps to hundreds of thousands of cps. The area of a radiation receiving portion of a TES is smaller than 1 $mm^2$ in general, and the maximum count rate of a TES is hundreds of cps to thousands of cps.

In an energy dispersive X-ray detector, in general, the counting efficiency and the energy resolution are in a trade-off relationship. In a Si semiconductor detector, such as a silicon drift type detector, which of energy resolution or counting efficiency priority is given to can also be selected by switching a time constant of a counting circuit within the range of the capability of the detector. In order to realize high energy resolution, a signal from the X-ray detector needs to be extracted with high accuracy. To this end, a time constant of a filter or the time for extracting one signal is extended. As a result, the counting efficiency is inevitably lowered. In contrast, in order to raise the counting efficiency, a method which makes the time constant of the filter short or a method which increases the speed of data processing without effectively utilizing all pieces of information of detection signals is known; however, in these methods, the energy resolution is deteriorated. Furthermore, a method which uses a detection element designed for high counting efficiency and makes the area or thickness of the radiation receiving portion of the X-ray detector large is also known; however, energy resolution is sacrificed to some extent.

In mapping of a sample irradiated with charged particle beams, a microanalysis in a bulk sample, or the like, high counting efficiency is required. However, if a silicon drift type detector having energy resolution of about 100 eV to 200 eV, or the like is used for an unknown sample, in a case where there is an element close to energy of characteristic X-rays, the type of element cannot be discriminated, and even if the counting efficiency is high, there is a problem in that the accuracy of quantitative analysis is degraded.

In regard to such a problem, hitherto, a method which performs quantitative analysis using an analysis device with high counting efficiency based on a result of performing qualitative analysis using an analysis device with high energy resolution in advance has been known (see Japanese Unexamined Patent Application, First Publication No. 2002-71591). The analysis device with high energy resolution is an analysis device which uses a TES, an STJ, or the like capable of realizing extremely high resolution by means of a superconductive phenomenon. The analysis device with high counting efficiency is an analysis device which uses a silicon drift type detector or the like. In this method, a detector with high counting efficiency and a detector with high energy resolution are integrated or provided separately, and analysis is performed such that the features of the respective detectors are utilized.

Hitherto, a method which improves detection efficiency using a superconducting X-ray detector with high energy resolution has been known (see D. A. WOLLMAN, and five other, "High-resolution, energy-dispersive microcalorimeter spectrometer for X-ray microanalysis", vol. 188, Pt 3, December 1997, pp. 196-223). In general, since a superconducting X-ray detector has a small detection area and low counting efficiency, in this method, X-rays are condensed on the detector using an optical element, whereby the small detection area is compensated for and the counting efficiency is improved.

RELATED ART DOCUMENT

Patent Document

[Patent Document 1] Japanese Unexamined Patent Application, First Publication No. 2002-71591

Non-Patent Document

[Non-Patent Document 1] D. A. WOLLMAN, and five other, "High-resolution, energy-dispersive microcalorimeter spectrometer for X-ray microanalysis", vol. 188, Pt 3, December 1997, pp. 196-223

SUMMARY OF THE INVENTION

However, as in the related art described above, in a case where two kinds of detectors are integrated, when performing a measurement with high energy resolution, X-rays which are incident on a detector with high counting efficiency become wasteful, and the counting efficiency of a detector with low counting efficiency is further deteriorated. In a case where two kinds of detectors are provided separately, the two kinds of detectors occupy two mounting ports, it is difficult to attach other analysis devices, and the expandability of an analysis device is sacrificed. In addition, in a case where, of superconducting detectors, an STJ with comparatively high counting efficiency and a TES with comparatively excellent energy resolution are attached in combination, in addition to the two mounting ports being occupied, there is a problem in that a plurality of refrigerators are required and costs and an installation space required for a device configuration are high.

As in the related art described above, in a case where X-rays are condensed using an optical element, since the maximum count rate of the detection element does not change, there is a concern that it may not be possible to improve the counting efficiency.

The invention has been accomplished in consideration of the above-described problems, and an object of the invention is to provide an X-ray analysis device capable of realizing detection with high energy resolution and detection with high counting efficiency without occupying a plurality of mounting ports.

In order to solve the above-described problems and to attain the object, the invention uses the following forms.

(1) An X-ray analysis device according to an aspect of the invention includes an excitation source which excites a sample to be analyzed to emit characteristic X-rays, a plurality of detection units which detect characteristic X-rays emitted from the sample, an optical member which guides the characteristic X-rays emitted from the sample to at least any one of the plurality of detection units, and a distance changing mechanism which changes the distance between each of the plurality of detection units and the optical member in an axial direction of an optical axis of the optical member. The plurality of detection units include at least a first detection unit and a second detection unit having different detection characteristics, the first detection unit is formed such that energy resolution is given relative priority over counting efficiency in contrast to the second detection unit, and the second detection unit is formed such that counting efficiency is given relative priority over energy resolution in contrast to the first detection unit.

According to the X-ray analysis device of the aspect described in (1), since the distance changing mechanism which changes the distance between the optical member and each of the first detection unit and the second detection unit is provided, in the first detection unit and the second detection unit, it is possible to switch between the regions which are primarily irradiated with the characteristic X-rays. With this, it is possible to perform analysis according to the detection characteristics of each of the first detection unit and the second detection unit. It is possible to perform analysis, in which energy resolution is given priority, using the first detection unit, and to perform analysis, in which counting efficiency is given priority, using the second detection unit.

(2) In the X-ray analysis device described in (1), either one of the first detection unit and the second detection unit may be disposed at a position relatively close to the optical axis, and the other of the first detection unit and the second detection unit may be disposed at a position relatively distant from the optical axis.

According to the X-ray analysis device of the aspect described in (2), in a case where the first detection unit in which energy resolution is given priority is disposed at a position close to the optical axis, and the distance between the first detection unit and the optical member substantially coincides with the focal distance of the optical member, it is possible to suitably perform analysis in which energy resolution is given priority. Furthermore, in a case where the second detection unit in which counting efficiency is given priority is disposed at a position close to the optical axis, and the distance between the second detection unit and the optical member substantially coincides with the focal distance of the optical member, it is possible to suitably perform analysis, such as microanalysis, in which counting efficiency is given priority.

(3) In the X-ray analysis device described in (2), the second detection unit may be disposed so that the surroundings of the first detection unit are surrounded.

According to the X-ray analysis device of the aspect described in (3), since the region irradiated with the characteristic X-rays passing through the optical member is changed according to the distance from the optical member, in the first detection unit and the second detection unit, it is possible to easily switch between the regions which are primarily irradiated with the characteristic X-rays by changing the distance between the optical member and each of the first detection unit and the second detection unit.

(4) In the X-ray analysis device described in any one of (1) to (3), the distance changing mechanism may realize a first state where the distance is set to a first distance such that an irradiation region of the characteristic X-rays guided by the optical member is included in an effective detection region of the first detection unit, and a second state where the distance is set to a second distance such that the irradiation region of the characteristic X-rays guided by the optical member is included in an effective detection region of the second detection unit.

According to the X-ray analysis device of the aspect described in (4), it is possible to perform analysis, in which energy resolution is given priority, in the first state, and to perform analysis, in which counting efficiency is given priority, in the second state.

(5) The X-ray analysis device described in any one of (1) to (4) may further include a dead time acquisition unit which acquires a dead time for the detection of the characteristic X-rays in the plurality of detection units, and the distance changing mechanism may change the distance so as to maintain the dead time to be less than a predetermined threshold.

According to the X-ray analysis device of the aspect described in (5), it is possible to maintain the dead time for the detection of the characteristic X-rays to be less than a predetermined value simply by changing the distance between the optical member and each of the first detection unit and the second detection unit.

(6) The X-ray analysis device described in any one of (1) to (4) may further include a frequency acquisition unit which acquires an overlap frequency of detection signals of the characteristic X-rays in the plurality of detection units, and the distance changing mechanism may change the distance so as to maintain the overlap frequency of the detection signals to be less than a predetermined threshold.

According to the X-ray analysis device of the aspect described in (6), it is possible to maintain the overlap frequency of the detection signals to be less than a predetermined value simply by changing the distance between the optical member and each of the first detection unit and the second detection unit.

According to the X-ray analysis device of the invention, since the distance changing mechanism which changes the distance between the optical member and each of the first detection unit and the second detection unit is provided, in the first detection unit and the second detection unit, it is possible to switch between the regions which are primarily irradiated with the characteristic X-rays. With this, it is possible to perform analysis according to the detection characteristics of each of the first detection unit and the second detection unit. It is possible to perform analysis, in which energy resolution is given priority, using the first detection unit, and to perform analysis, in which counting efficiency is given priority, using the second detection unit.

DETAILED DESCRIPTION OF THE INVENTION

Hereinafter, an X-ray analysis device according to an embodiment of the invention will be described referring to the accompanying drawings.

An X-ray analysis device 10 of this embodiment is usable as, for example, a composition analysis device, such as an electron microscope, an ion microscope, an X-ray microscope, or a fluorescent X-ray analysis device.

Figure 1:
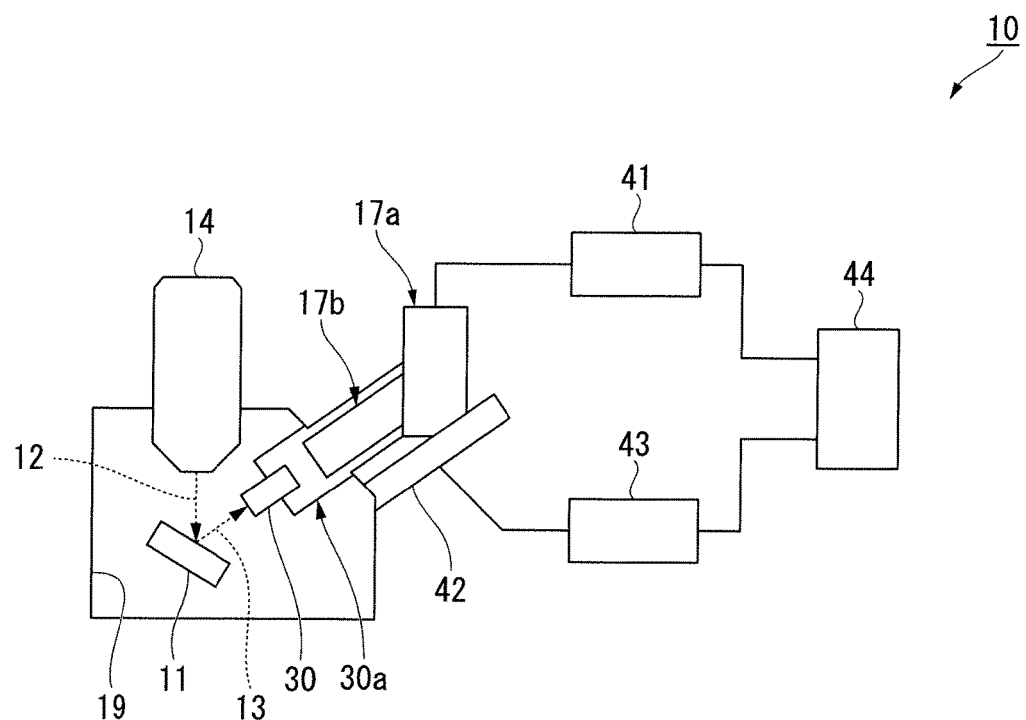
FIG. 1 is a diagram schematically showing the configuration of an X-ray analysis device according to an embodiment of the invention.
Figure 2:
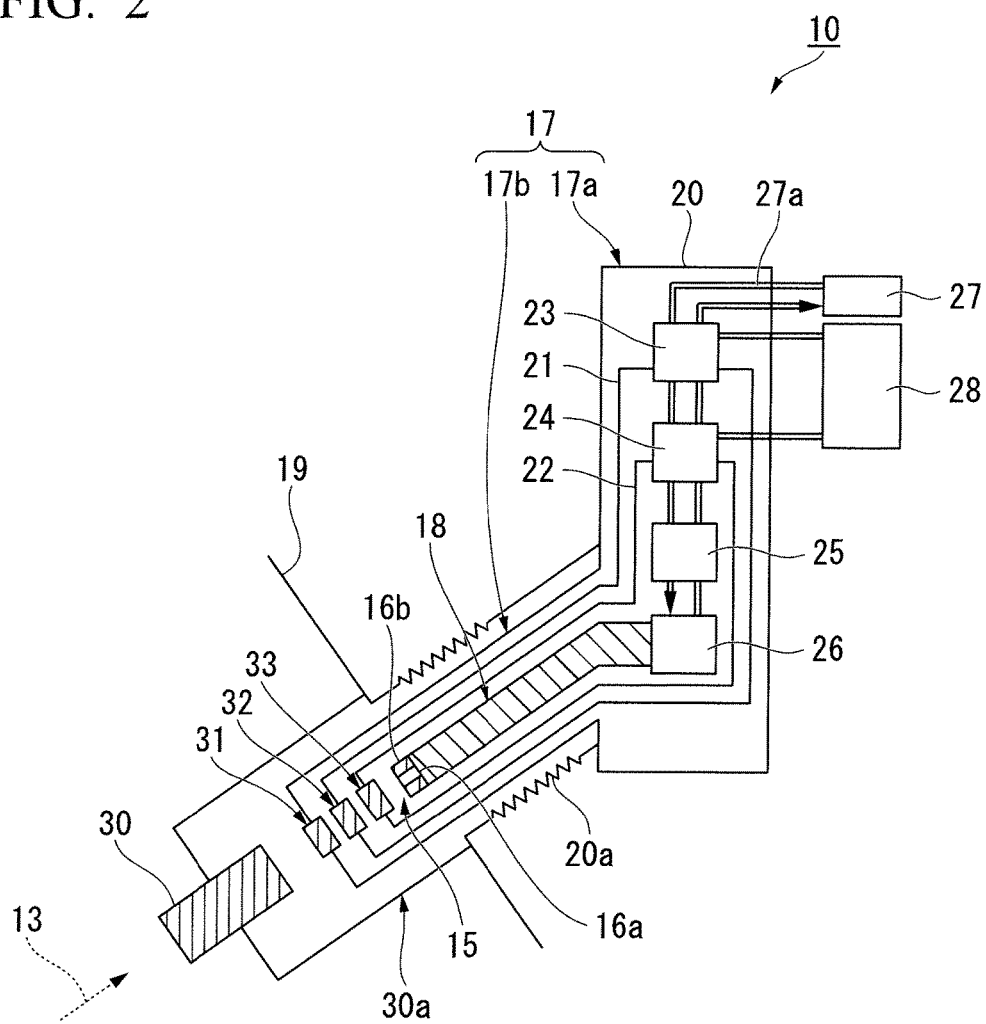
FIG. 2 is a sectional view schematically showing the configuration of a cooling unit in the X-ray analysis device according to the embodiment of the invention.

As shown in FIGS. 1 and 2, the X-ray analysis device 10 includes an electron gun 14 which irradiates a sample 11 to be analyzed with an electron beam 12 to excite the sample 11, and an X-ray detector 15 which detects characteristic X-rays 13 emitted from the excited sample 11.

The X-ray detector 15 includes a first detection unit 16a and a second detection unit 16b which have, for example, a superconducting transition edge sensor (Transition Edge Sensor, TES) as an X-ray detection unit.

The TES uses superconducting transition of a superconductor, and maintains an operation point in an intermediate state between normal conductor and superconduction in an X-ray detection operation. With this, in a case where a single X-ray is absorbed into the TES, change in resistance of several mΩ is obtained with respect to, for example, variation in temperature of 100 μK in a state where the operation point is maintained during superconducting transition, and a radiation pulse of μA order can be obtained. If data determining the relationship between a pulse peak value and the energy of radiation is stored in advance, even if the TES is irradiated with radiation having unknown energy, it is possible to detect the energy of incident radiation from the signal pulse peak value.

The first detection unit 16a is constituted of a TES which is formed so as to give priority to energy resolution over counting efficiency. The TES which is formed so as to give priority to energy resolution includes, for example, a detection element which is formed of a material for giving priority to energy resolution, or the like, and is formed such that at least one of the light receiving area or the thickness of the detection element is relatively smaller than that of the second detection unit 16b. The second detection unit 16b is constituted of a TES which is formed so as to give priority to counting efficiency over energy resolution. The TES which is formed so as to give priority to counting efficiency includes, for example, a detection element which is formed of a material for giving priority to counting efficiency, or the like, and is formed such that at least one of the area or the thickness of the detection element is relatively greater than that of the first detection unit 16a.

Figure 3:
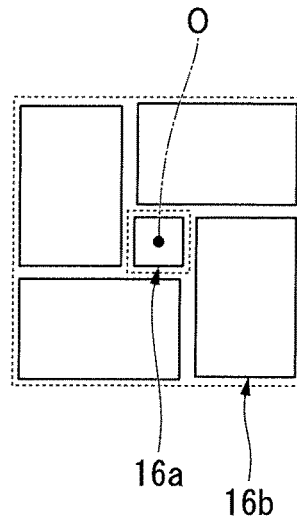
FIG. 3 is a plan view of a first detection unit and a second detection unit of the X-ray analysis device according to the embodiment of the invention when viewed from a direction along an optical axis of an X-ray optical member.

For example, as shown in FIG. 3, the first detection unit 16a is disposed such that the surroundings there of is surrounded by the second detection unit 16b. The first detection unit 16a is constituted of, for example, a single TES disposed in a central portion of an X-ray receiving region formed by the first detection unit 16a and the second detection unit 16b. The first detection unit 16a is disposed in a region including the optical axis O of the X-ray optical member 30.

The second detection unit 16b is constituted of a plurality of TESs (for example, four TESs) segmented in the surroundings of the first detection unit 16a. The second detection unit 16b is disposed in a region separated from the optical axis O of the X-ray optical member 30.

As shown in FIG. 2, the X-ray analysis device 10 includes a cooling unit 17 which cools the first detection unit 16a and the second detection unit 16b.

The cooling unit 17 has a refrigerator body 17a, and a snout 17b which is mounted in the refrigerator body 17a and has a heat insulation structure. The cold head 18 is disposed inside the snout 17b. The first detection unit 16a and the second detection unit 16b are provided at the tip of the cold head 18 inside the snout 17b.

The cooling unit 17 is attached to a single mounting port of a chamber 19 by a tubular portion 20a having a bellows part. The inside of each of the surrounding shield 20, the snout 17b, and the chamber 19 is evacuated by a turbomolecular pump, a diffusion pump, or the like. The degree of vacuum of the inside of each of the surrounding shield 20, the snout 17b, and the chamber 19 is, for example, about $10^{-3}$ to $10^{-5}$ Pa.

The refrigerator body 17a is, for example, a dilution refrigerator, an adiabatic demagnetization refrigerator, or the like. A dilution refrigerator performs cooling using an enthalpy difference when 3He is melted from a dense phase to a dilute phase inside a mixing chamber. The adiabatic demagnetization refrigerator aligns the directions of spins by applying a magnetic field to a magnetic substance, and cools an object connected to the magnetic substance with an increase in entropy when eliminating the magnetic field.

For example, the refrigerator body 17a which is a dilution refrigerator includes a surrounding shield 20, a first heat shield 21, a second heat shield 22, a first pot 23, a second pot 24, a still 25, a mixer (mixing chamber) 26, a gas circulator 27, and a pre-cooler 28.

A part of each of the surrounding shield 20, the first heat shield 21, and the second heat shield 22 is formed in a shape extending so as to cover the cold head 18, thereby constituting the snout 17b.

The surrounding shield 20 stores the first heat shield 21 therein. The first heat shield 21 stores the second heat shield 22 therein.

The surrounding shield 20 and the chamber 19 are connected by the tubular portion 20a having a bellows part. The tubular portion 20a expands and contracts in a case where the snout 17b is moved by a distance changing mechanism 42 described below along with the whole of the refrigerator body 17a or a part of the refrigerator body 17a movable while maintaining performance.

The first pot 23 is provided in the first heat shield 21 inside the surrounding shield 20. The second pot 24 is provided in the second heat shield 22 inside the first heat shield 21. The still 25 and the mixer 26 are stored inside the second heat shield 22. The cold head 18 is connected to the mixer 26.

The gas circulator 27 is disposed outside the surrounding shield 20. The gas circulator 27 is connected to a gas circulation flow passage 27a which is disposed inside the surrounding shield 20, and circulates 3He in the gas circulation flow passage 27a. The first pot 23, the second pot 24, the still 25, and the mixer 26 are connected to the gas circulation flow passage 27a.

The pre-cooler 28 is disposed outside the surrounding shield 20. The pre-cooler 28 is connected to the first pot 23 and the second pot 24. The pre-cooler 28 is, for example, a mechanical refrigerator, such as a GM refrigerator.

The first pot 23 is cooled to, for example, about 20 K by the pre-cooler 28. The first pot 23 cools the first heat shield 21.

The second pot 24 is cooled to, for example, about 1 K by the pre-cooler 28. The second pot 24 cools the second heat shield 22.

The first pot 23 and the second pot 24 liquefy 3He of the gas circulation flow passage 27a.

The still 25 vaporizes (fractionates) 3He in the dilute phase. The still 25 is maintained, for example, at about 0.7 K less than 1 K.

The mixer 26 moves 3He from the dense phase to the dilute phase. The mixer 26 is maintained, for example, at about 100 mK. The mixer 26 cools the cold head 18 near to 100 mK.

The temperature of the surrounding shield 20 is an atmosphere temperature (for example, 27° C. which is a room temperature, or the like).

The X-ray optical member 30 which causes the characteristic X-rays 13 emitted from the sample 11 to pass toward the first detection unit 16a and the second detection unit 16b is supported by an X-ray optical member fixing portion 30a. The X-ray optical member fixing portion 30a is fixed to the chamber 19. The X-ray optical member 30 is, for example, a capillary which is provided with a through hole allowing the characteristic X-rays 13 to pass therethrough. A material of the capillary is a non-metal or a metal, and is constituted of, for example, a plurality of glass thin tubes. The X-ray optical member 30 has a function of condensing the characteristic X-rays 13 emitted from the sample 11 at a predetermined focal distance and a focus diameter. The X-ray optical member 30 may condense the characteristic X-rays 13 using, for example, refraction, reflection, or the like of the characteristic X-rays 13.

In the snout 17b, the surrounding shield 20 is disposed between the tubular portion 20a and the first heat shield 21. The surrounding shield 20 includes a surrounding X-ray window 31 for allowing the characteristic X-rays 13 emitted from the sample 11 to reach the first detection unit 16a and the second detection unit 16b. The surrounding X-ray window 31 includes, for example, laminated aluminum film and insulating film.

In the snout 17b, the first heat shield 21 is disposed between the surrounding shield 20 and the second heat shield 22. The first heat shield 21 includes a first X-ray window 32 for allowing the characteristic X-rays 13 emitted from the sample 11 to reach the first detection unit 16a and the second detection unit 16b. The first X-ray window 32 includes, for example, laminates aluminum film and insulating film In the snout 17b, the second heat shield 22 is disposed between the first heat shield 21 and the cold head 18. The second heat shield 22 includes a second X-ray window 33 for allowing the characteristic X-rays 13 emitted from the sample 11 to reach the first detection unit 16a and the second detection unit 16b. The second X-ray window 33 includes, for example, laminated aluminum film and insulating film.

In the snout 17b, the first heat shield 21 and the second heat shield 22 transmit the characteristic X-rays 13 emitted from the sample 11 to the cold head 18, and shield heat radiation from the surrounding shield 20.

As shown in FIG. 1, the X-ray analysis device 10 includes a processing unit 41, a distance changing mechanism 42 which moves the position of the snout 17b along with the whole of the refrigerator body 17a or a part of the refrigerator body 17a movable while maintaining performance, a drive unit 43, and a control unit 44.

A plurality of processing units 41 are provided, for example, for a plurality of respective TESs of the first detection unit 16a and the second detection unit 16b shown in FIG. 3. The processing units 41 multiplex and process signals from a plurality of TESs. Multiplexing of the signals of a plurality of TESs in the processing unit 41 is, for example, time division multiplexing, frequency multiplexing, code multiplexing, multiplexing using resonance, or the like.

Figure 4:
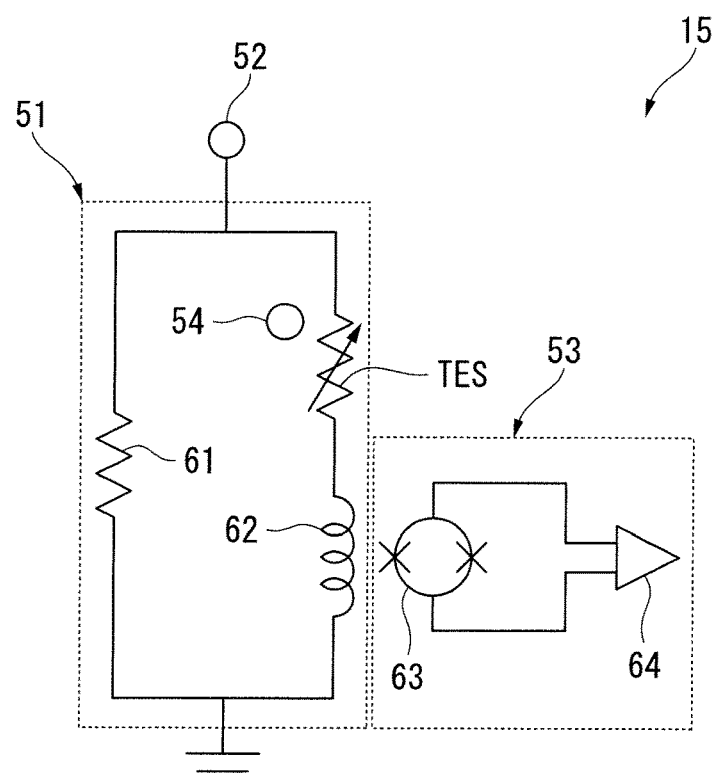
FIG. 4 is a diagram showing the configuration of an X-ray detector of the X-ray analysis device according to the embodiment of the invention.

For example, as shown in FIG. 4, a general configuration of the X-ray detector 15 using a TES for an X-ray detection unit includes a sensor circuit unit 51, a bias current source 52, a current detection mechanism 53, and a thermometer 54. If radiation is received, the TES detects the energy of radiation as change in temperature and outputs the change in temperature as a current signal. The sensor circuit unit 51 is connected to the TES. The bias current source 52 makes a current for simulatively driving the sensor circuit unit 51 at a constant voltage flow in the sensor circuit unit 51. The current detection mechanism 53 detects the current flowing in the TES. The thermometer 54 is incorporated inside a pedestal (not shown) for installing the sensor circuit unit 51 provided inside the cold head 18 or in the tip portion of the cold head 18, and measures the temperature of the cold head 18 or the pedestal in which the TES is provided. A signal of the temperature output from the thermometer 54 is used in processing for maintaining the temperature of the cold head 18 or the pedestal constant and processing, such as detection sensitivity correction of the TES.

The sensor circuit unit 51 includes a shunt resistor 61 which has a resistance value smaller than the TES and is connected in parallel to the TES, and an input coil 62 which is connected in series to the TES. In the sensor circuit unit 51, if a bias current flows from the bias current source 52, a current is branched at a resistance ratio of the resistance value of the shunt resistor 61 and the resistance value of the TES. That is, a voltage value of the TES is determined by a current flowing in the shunt resistor 61 and a voltage determined by the resistance value of the shunt resistor 61.

The current detection mechanism 53 includes an SQUID amplifier 63, and a room temperature amplifier 64 which amplifies and shapes an electrical signal output from the SQUID amplifier 63. Although the SQUID amplifier 63 using the input coil 62 and the room temperature amplifier 64 are used as the current detection mechanism 53, other configurations may be used as long as change in current flowing in the TES can be detected. A signal output from the room temperature amplifier 64 is input to a peak analyzer (not shown) which obtains a peak value (voltage value) of a signal pulse and generates an energy spectrum, or the like.

The distance changing mechanism 42 moves the first detection unit 16a and the second detection unit 16b so as to change the distance between the X-ray optical member 30 and each of the first detection unit 16a and the second detection unit 16b using drive force output from the drive unit 43 or drive force input by an operator's operation. The distance changing mechanism 42 includes, for example, a rack and pinion mechanism, a linear motor mechanism, a ball screw mechanism, or the like. The distance changing mechanism 42 moves the first detection unit 16a and the second detection unit 16b to the front and the rear and back with respect to the X-ray optical member 30 in a predetermined emission direction of the characteristic X-rays 13 emitted from the sample 11. The distance changing mechanism 42 changes the relative distance from the X-ray optical member 30, which condenses the characteristic X-rays 13 at a predetermined focal distance and a focus diameter, to each of the first detection unit 16a and the second detection unit 16b, thereby changing the irradiation region of the characteristic X-rays 13 in the first detection unit 16a and the second detection unit 16b.

Figure 5:
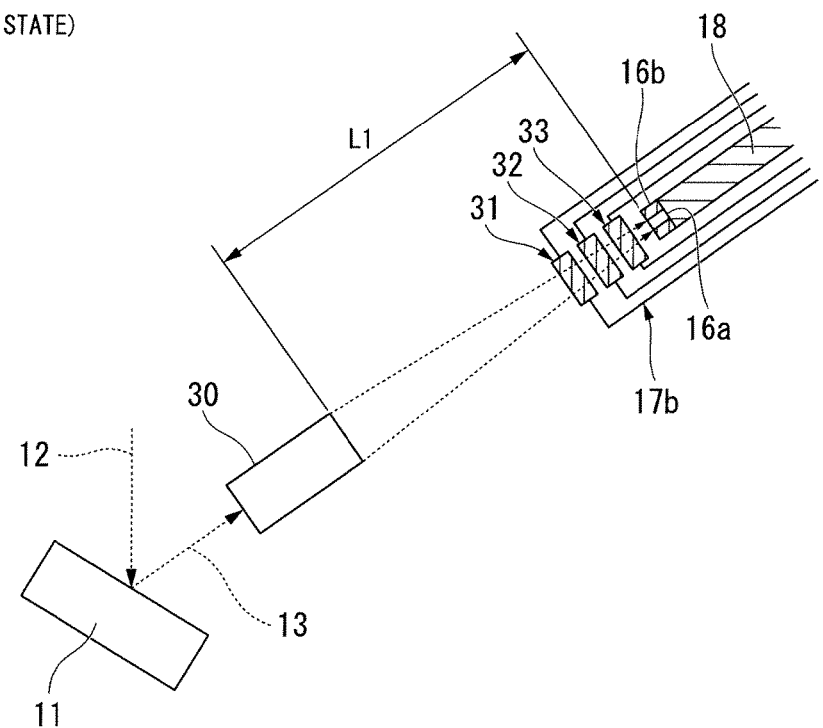
FIG. 5 is a diagram showing an example of the relative positions of the X-ray optical member and each of the first detection unit and the second detection unit of the X-ray analysis device according to the embodiment of the invention.
Figure 5:
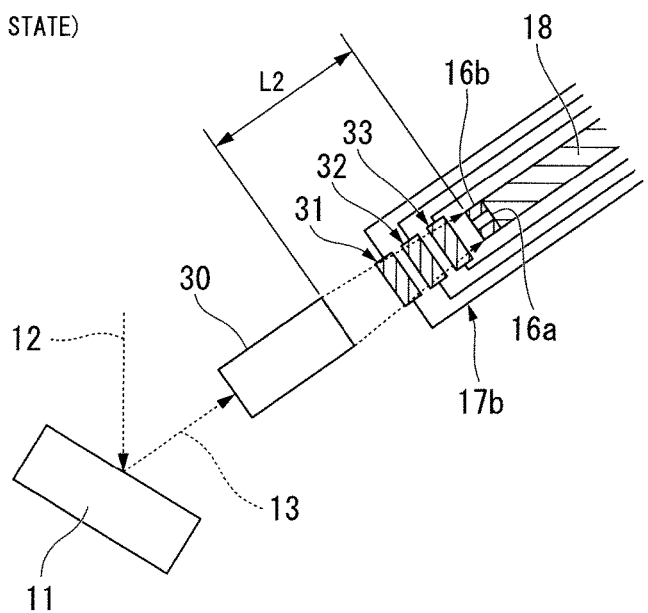

The distance changing mechanism 42 makes the irradiation region of the characteristic X-rays 13 substantially coincide with the effective detection region of the first detection unit 16a, for example, as shown in FIG. 5, in a first state where the distance from the X-ray optical member 30 to each of the first detection unit 16a and the second detection unit 16b is set to a first distance L1. In the first state, the distance changing mechanism 42 makes the focus diameter of the characteristic X-rays 13 condensed by the X-ray optical member 30 substantially coincide with the outside dimension of the first detection unit 16a. In the first state, the distance changing mechanism 42 condenses the characteristic X-rays 13 on the first detection unit 16a in which energy resolution is given priority over counting efficiency.

The distance changing mechanism 42 makes the irradiation region of the characteristic X-rays 13 substantially coincide with the effective detection region of the first detection unit 16a and the second detection unit 16b, for example, in a second state where the distance from the X-ray optical member 30 to each of the first detection unit 16a and the second detection unit 16b is set to a second distance L2 (<first distance L1). In the second state, the distance changing mechanism 42 makes the focus diameter of the characteristic X-rays 13 condensed by the X-ray optical member 30 substantially coincide with the outside dimension of the second detection unit 16b. In the second state, the distance changing mechanism 42 condenses the characteristic X-rays 13 on at least the whole of the second detection unit 16b in which counting efficiency is given priority over energy resolution.

The drive unit 43 includes, for example, a motor or the like. The drive unit 43 generates drive force for driving the distance changing mechanism 42.

The control unit 44 integrally controls the X-ray analysis device 10. The control unit 44 includes a processor, such as a CPU, a ROM for storing a program, a RAM for temporarily storing data, and the like.

The control unit 44 controls the operation of a peak analyzer (not shown) which generates an energy spectrum, a spectrum display unit (not shown) which displays an energy spectrum, or the like using a signal output from the processing unit 41.

The control unit 44 controls the distance changing mechanism 42 and the drive unit 43, for example, according to a direct instruction of an operator to the operation of the distance changing mechanism 42, a predetermined analysis processing operation stored in advance, the state of X-ray detection in the first detection unit 16a and the second detection unit 16b, or the like. The control unit 44 controls the distance changing mechanism 42, for example, according to an instruction input from the operator who operates an operation member, such as a switch, and changes the distance from the X-ray optical member 30 to each of the first detection unit 16a and the second detection unit 16b. The control unit 44 automatically controls the distance changing mechanism 42, for example, according to the flow of a predetermined analysis processing operation set in advance, and changes the distance from the X-ray optical member 30 to each of the first detection unit 16a and the second detection unit 16b. The control unit 44 appropriately changes energy resolution and counting efficiency obtained by the first detection unit 16a and the second detection unit 16b based on, for example, control data stored in advance. Control data stored in advance is data indicating the correlation between a distance changeable by the distance changing mechanism 42 and energy resolution and counting efficiency obtained by the first detection unit 16a and the second detection unit 16b, or the like. Control unit 44 changes the distance using the distance changing mechanism 42 based on control data stored in advance according to the purpose of analysis processing, thereby automatically changing energy resolution and counting efficiency stepwise or continuously.

The control unit 44 acquires a dead time of X-ray detection in the first detection unit 16a and the second detection unit 16b based on, for example, a signal output from the processing unit 41. The control unit 44 changes the distance from the X-ray optical member 30 to each of the first detection unit 16a and the second detection unit 16b so as to maintain the dead time of X-ray detection to be less than a predetermined threshold. The control unit 44 acquires the overlap frequency of the detection signals of X-ray detection in the first detection unit 16a and the second detection unit 16b based on, for example, a signal output from the processing unit 41. The control unit 44 changes the distance from the X-ray optical member 30 to each of the first detection unit 16a and the second detection unit 16b so as to maintain the overlap frequency of the detection signals to be less than a predetermined threshold.

Hereinafter, the operation of the X-ray analysis device 10 of the above-described embodiment will be described.

The X-ray analysis device 10 executes, for example, three different analysis processing operations. The three analysis processing operations are low energy analysis, a fast analysis, and microanalysis.

In the low energy analysis, analysis of micro regions or analysis of micro particles near the surface of the sample 11, or the like is performed by irradiating the sample 11 with a low-acceleration voltage electron beam 12. In the analysis of the characteristic X-rays 13 generated by the irradiation of the low-acceleration voltage electron beam 12, since spectrums of many elements are densely distributed, high energy resolution is required. In addition, for reasons of improvement of resolution of analysis, reduction of damage to the sample, and the like, in many cases, analysis using a low-current electron beam 12 is required.

Figure 12:
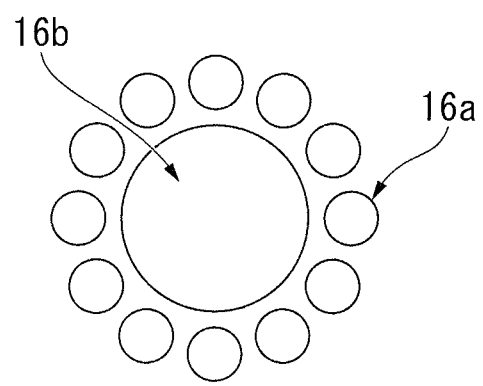
FIG. 12 is a plan view of a first detection unit and a second detection unit of an X-ray analysis device according to a sixth modification example of the embodiment of the invention when viewed from a direction along an optical axis of an X-ray optical member.

In the analysis using the low-current electron beam 12, the characteristic X-rays to be generated are reduced. In a case of the low energy analysis, in a case where the first detection unit 16a and the second detection unit 16b are disposed as shown in FIG. 3, the control unit 44 controls the distance changing mechanism 42 such that the distance from the X-ray optical member 30 to each of the first detection unit 16a and the second detection unit 16b becomes the first distance L1. With this, in the low energy analysis, the control unit 44 condenses the characteristic X-rays 13 on the first detection unit 16a in which energy resolution is given priority. In a case where the first detection unit 16a and the second detection unit 16b are disposed as shown in FIG. 12 described below, the control unit 44 controls the distance changing mechanism 42 such that the distance from the X-ray optical member 30 to each of the first detection unit 16a and the second detection unit 16b becomes the second distance L2. With this, in the low energy analysis, the control unit 44 condenses the characteristic X-rays 13 on at least the whole of the first detection unit 16a in which energy resolution is given priority. With this, in the low energy analysis with a smaller amount of X-rays, the control unit 44 condenses the characteristic X-rays 13 on the first detection unit 16a in which energy resolution is given priority.

In the fast analysis, analysis is performed by measuring the characteristic X-rays 13 at a high count rate, for example, like qualitative analysis and mapping, and the like. In a case of the fast analysis, in a case where the first detection unit 16a and the second detection unit 16b are disposed as shown in FIG. 3, the control unit 44 controls the distance changing mechanism 42 such that the distance from the X-ray optical member 30 to each of the first detection unit 16a and the second detection unit 16b becomes the second distance L2. With this, the control unit 44 condenses the characteristic X-rays 13 on at least the whole of the second detection unit 16b in which counting efficiency is given priority. In a case where the first detection unit 16a and the second detection unit 16b are disposed as shown in FIG. 12 described below, the control unit 44 controls the distance changing mechanism 42 such that the distance from the X-ray optical member 30 to each of the first detection unit 16a and the second detection unit 16b becomes the first distance L1.

With this, in the fast analysis, the control unit 44 condenses the characteristic X-rays 13 on the second detection unit 16b in which counting efficiency is given priority.

The microanalysis is, for example, analysis in a case where there are elements which are behind the spectrums of principal elements since the amount thereof is very small. In a case of the microanalysis, the control unit 44 condenses the characteristic X-rays 13 on the whole of the first detection unit 16a and the second detection unit 16b or at least a part of each of the first detection unit 16a and the second detection unit 16b in order to prevent the generation of an inadvertence of a quantification target by improving quantification accuracy of an analysis result. For example, in a case where the first detection unit 16a and the second detection unit 16b are disposed as shown in FIG. 3 or FIG. 12 described below, the control unit 44 controls the distance changing mechanism 42 such that the distance from the X-ray optical member 30 to each of the first detection unit 16a and the second detection unit 16b becomes the second distance L2.

In case of the microanalysis, the control unit 44 may perform a measurement using the first detection unit 16a and the second detection unit 16b simultaneously or sequentially. The control unit 44 may improve the quantification accuracy of an analysis result with high counting efficiency in the second detection unit 16b, in which counting efficiency is given priority, based on, for example, an analysis result with high energy resolution in the first detection unit 16a in which energy resolution is given priority. In a case where the first detection unit 16a and the second detection unit 16b are as shown in FIG. 3, the control unit 44 may first perform qualitative analysis while setting the distance from the X-ray optical member 30 to each of the first detection unit 16a and the second detection unit 16b to the first distance L1, and next, may perform quantitative analysis while setting the distance to the second distance L2. In a case where the first detection unit 16a and the second detection unit 16b are disposed as shown in FIG. 12 described below, the control unit 44 may perform qualitative analysis while setting the distance from the X-ray optical member 30 to each of the first detection unit 16a and the second detection unit 16b to the second distance L2, and next, may perform quantitative analysis while setting the distance to the first distance L1.

As described above, according to the X-ray analysis device 10 of the embodiment, since the distance changing mechanism 42 which changes the distance between the X-ray optical member 30 and each of the first detection unit 16a and the second detection unit 16b is provided, in the first detection unit 16a and the second detection unit 16b, it is possible to switch between the regions which are primarily irradiated with the characteristic X-rays 13. With this, it is possible to perform analysis according to the detection characteristics of each of the first detection unit 16a and the second detection unit 16b. It is possible to perform analysis, in which energy resolution is given priority, using the first detection unit 16a, and to perform analysis, in which counting efficiency is given priority, using the second detection unit 16b. Furthermore, it is possible to perform different analyses using the first detection unit 16a and the second detection unit 16b having different detection characteristics in a single mounting port of the chamber 19, to prevent an increase in costs required for a device configuration, and to prevent an increase in size of the device.

Hereinafter, modification examples of the above-described embodiment will be described.

In the above-described embodiment, although the X-ray analysis device 10 includes the distance changing mechanism 42 which changes the distance from the X-ray optical member 30 to each of the first detection unit 16a and the second detection unit 16b, the invention is not limited thereto.

Figure 6:
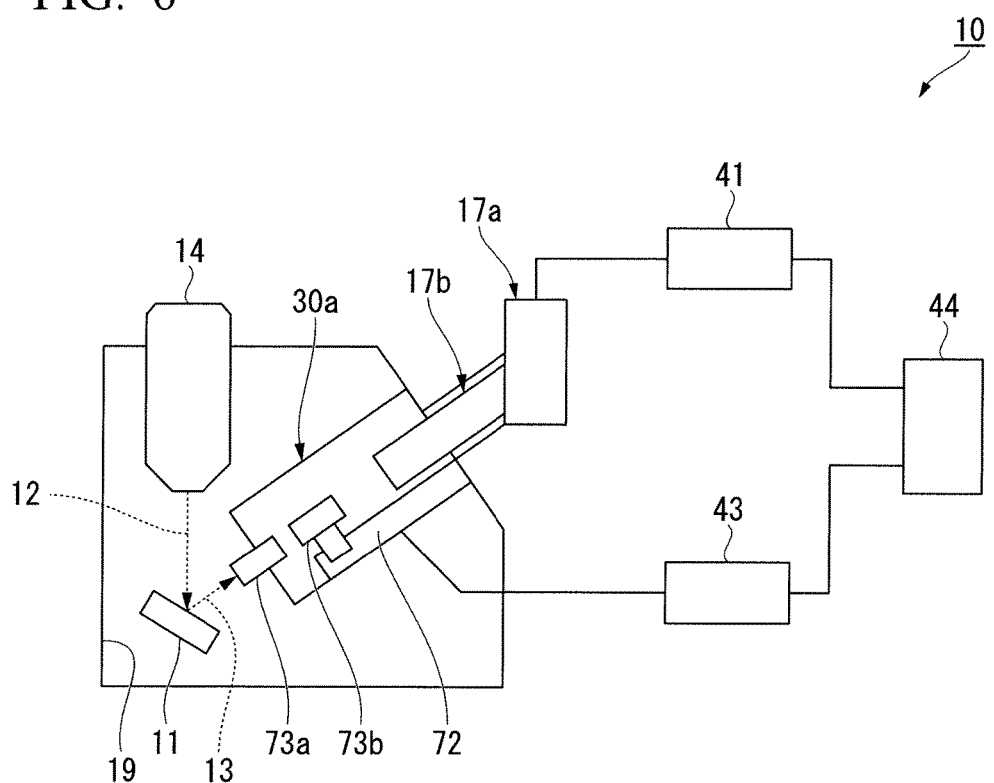
FIG. 6 is a diagram showing an example of the relative positions of each of a first X-ray optical member and a second X-ray optical member and each of a first detection unit and a second detection unit in an X-ray analysis device according to a first modification example of the embodiment of the invention.

In a first modification example of the above-described embodiment, instead of the distance changing mechanism 42, a distance changing mechanism 72 which changes the distance from each of the first detection unit 16a and the second detection unit 16b to the X-ray optical member 30 may be provided. For example, an X-ray analysis device 10 of the first modification example shown in FIG. 6 includes a first X-ray optical member 73a and a second X-ray optical member 73b as the X-ray optical member 30, and a distance changing mechanism 72 which moves the second X-ray optical member 73b. The first X-ray optical member 73a and the second X-ray optical member 73b are disposed such that the optical axes thereof are set to be coaxial. The first X-ray optical member 73a is fixed to a tip portion of an X-ray optical member fixing portion 30a at a given distance from the sample 11 from which the characteristic X-rays 13 are detected. The first X-ray optical member 73a is a point-to-parallel optical member, parallelizes a plurality of characteristic X-rays 13 radially emitted from the sample 11, and emits the characteristic X-rays 13 toward the second X-ray optical member 73b. The second X-ray optical member 73b is disposed between the first X-ray optical member 73a and each of the first detection unit 16a and the second detection unit 16b inside the snout 17b, and is connected to the distance changing mechanism 72. The distance changing mechanism 72 changes the distance from each of the first detection unit 16a and the second detection unit 16b to the second X-ray optical member 73b. The second X-ray optical member 73b is a parallel-to-point optical member, and focuses a plurality of characteristic X-rays 13 emitted in parallel from the first X-ray optical member 73a toward the X-ray detector 15. The focus diameter of the characteristic X-rays 13 from the second X-ray optical member 73b is changed by the distance changing mechanism 72. The distance changing mechanism 72 makes the irradiation region of the characteristic X-rays 13 substantially coincide with the effective detection region of the first detection unit 16a in the first state.

The distance changing mechanism 72 makes the irradiation region of the characteristic X-rays 13 substantially coincide with the effective detection region of the first detection unit 16a and the second detection unit 16b in the second state.

In addition to the distance changing mechanism 42 which changes the distance from the X-ray optical member 30 to each of the first detection unit 16a and the second detection unit 16b, the distance changing mechanism 72 which changes the distance from each of the first detection unit 16a and the second detection unit 16b to the X-ray optical member 30 may be further provided. In this case, the position of the X-ray optical member 30 and the position of each of the first detection unit 16a and the second detection unit 16b may be respectively changed.

In the above-described embodiment, although the distance changing mechanism 42 includes the drive unit 43, the invention is not limited thereto.

Instead of the drive unit 43, an operation unit which is used by an operator to change the distance between the X-ray optical member 30 and each of the first detection unit 16a and the second detection unit 16b by manually moving the first detection unit 16a and the second detection unit 16b to two or three or more positions set in advance may be provided. The above-described distance changing mechanism 72 may include a drive unit having a motor or the like, or an operation unit which receives a manual operation of the operator.

Figure 7:
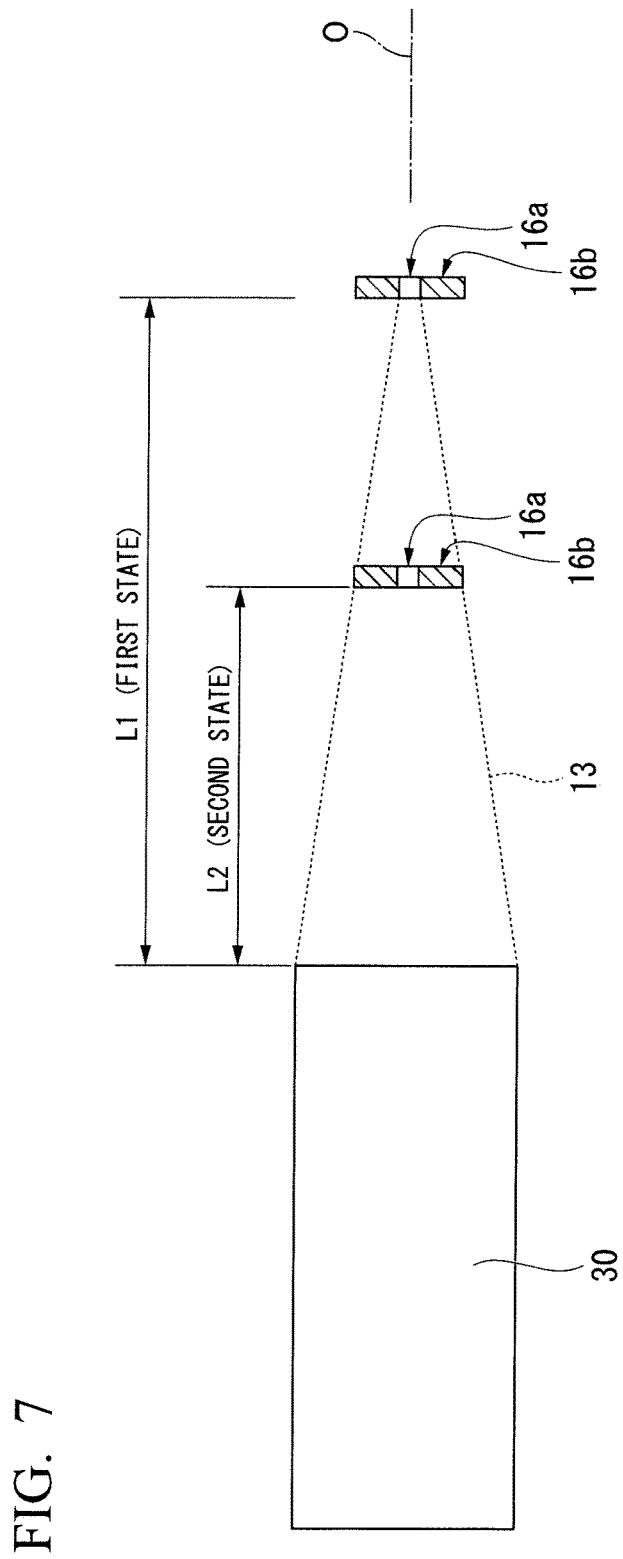
FIG. 7 is a diagram showing an example of the relative positions of the X-ray optical member and each of the first detection unit and the second detection unit in the X-ray analysis device according to the embodiment of the invention.

In the above-described embodiment, as shown in FIG. 7, although the X-ray analysis device 10 is configured such that the relative distances of the first detection unit 16a and the second detection unit 16b in the axial direction of the optical axis O with respect to the X-ray optical member 30 are the same, the invention is not limited thereto.

The first detection unit 16a and the second detection unit 16b may be disposed at positions deviated from each other in the axial direction of the optical axis O of the X-ray optical member 30. In this case, it is possible to make the size of a detection element close to the focal distance of the X-ray optical member 30 smaller than that in the above-described embodiment while securing the same effective area.

Figure 8:
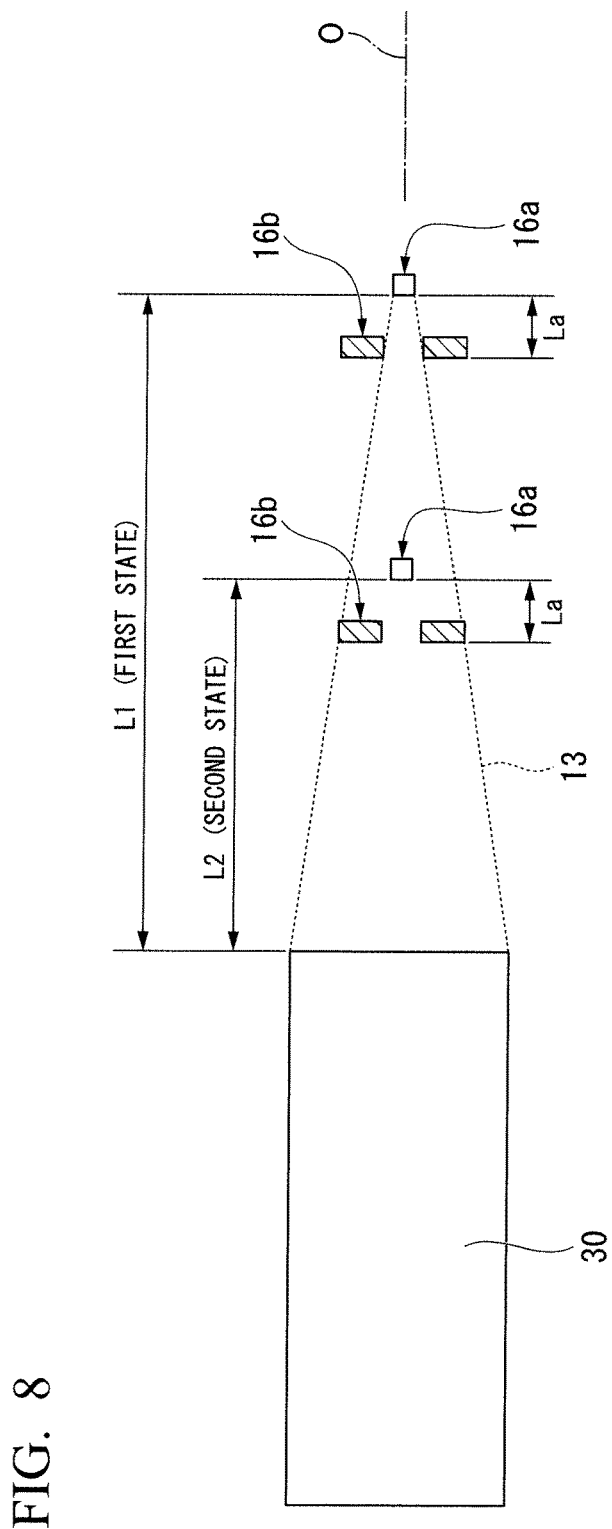
FIG. 8 is a diagram showing an example of the relative positions of an X-ray optical member and each of a first detection unit and a second detection unit in an X-ray analysis device according to a second modification example of the embodiment of the invention.

In a second modification example of the above-described embodiment, as shown in FIG. 8, a second detection unit 16b is disposed at a position closer to the X-ray optical member 30 by a predetermined distance La in the axial direction of the optical axis O than the first detection unit 16a. In the second modification example, the second detection unit 16b which is disposed separately from the optical axis O is operated as a collimator for the first detection unit 16a which is disposed on the optical axis O. In this case, even in a case where there is a region with no sensitivity to the characteristic X-rays 13 between the first detection unit 16a in which energy resolution is given priority and the second detection unit 16b in which counting efficiency is given priority, it is possible to make the total amount of the characteristic X-rays 13 incident on the first detection unit 16a and the second detection unit 16b equal to that in the above-described embodiment.

According to this second modification example, it is possible to easily secure a wiring space for each of the first detection unit 16a and the second detection unit 16b.

Figure 9:
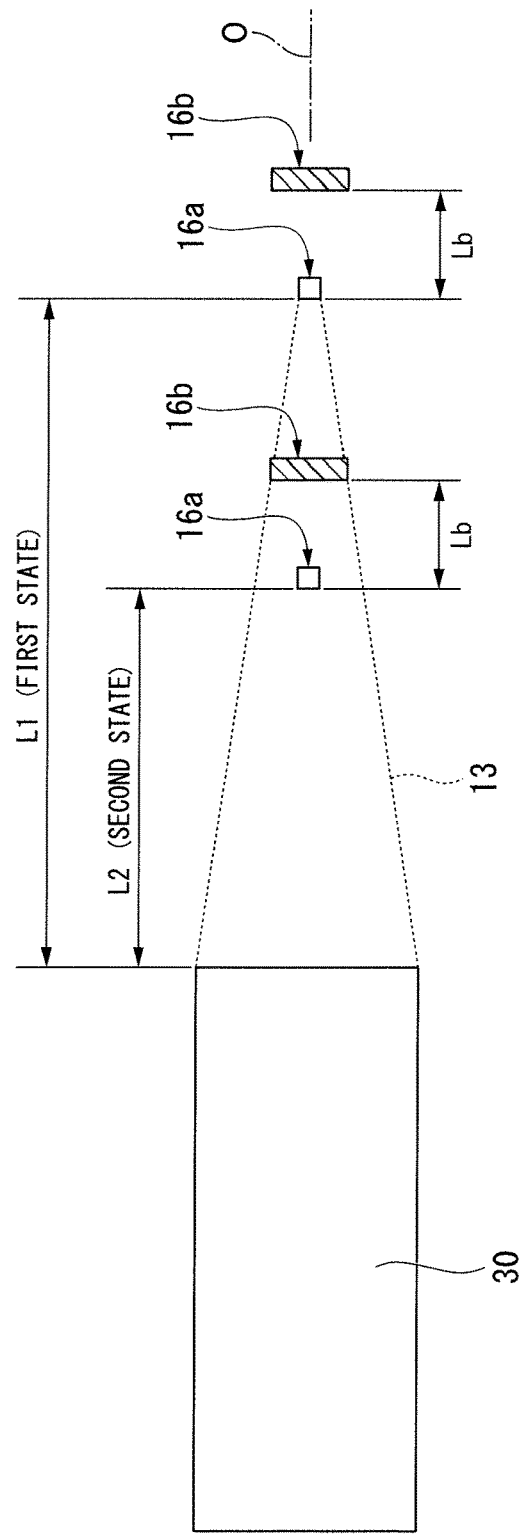
FIG. 9 is a diagram showing an example of the relative positions of an X-ray optical member and each of a first detection unit and a second detection unit in an X-ray analysis device according to a third modification example of the embodiment of the invention.

In a third modification example of the above-described embodiment, as shown in FIG. 9, a second detection unit 16b is disposed at a position more distant from the X-ray optical member 30 by a predetermined distance Lb in the axial direction of the optical axis O than the first detection unit 16a. In the third modification example, the first detection unit 16a which is disposed on the optical axis O is operated as a mask for the second detection unit 16b. In this case, it is possible to make the effective detection area of the second detection unit 16b, in which counting efficiency is given priority, smaller than that in the above-described embodiment while maintaining the total amount of the characteristic X-rays 13 incident on the first detection unit 16a and the second detection unit 16b to be equal to that in the above-described embodiment.

According to the third modification example, it is possible to eliminate the need for providing a space for disposing the first detection unit 16a in the central portion (that is, a region within a predetermined range including the optical axis O) of the second detection unit 16b. Furthermore, X-ray detectors which are different in size and performance may be disposed along the optical axis O so as to overlap each other.

In the X-ray analysis device 10 of the above-described embodiment, although the X-ray detector 15 includes the first detection unit 16a and the second detection unit 16b, the invention is not limited thereto.

Figure 10:
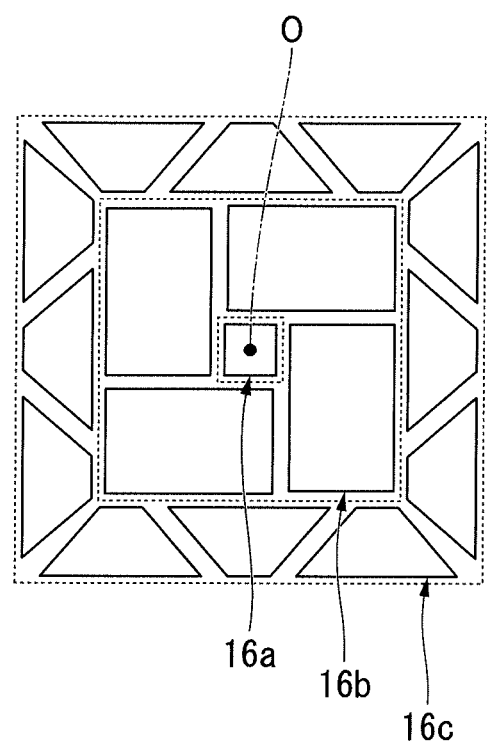
FIG. 10 is a plan view of a first detection unit and a second detection unit in an X-ray analysis device according to a fourth modification example of the embodiment of the invention when viewed from a direction along an optical axis of an X-ray optical member.

In a fourth modification example of the above-described embodiment, an X-ray detector 15 may include three or more detection units having different detection characteristics. In the fourth modification example of the above-described embodiment, as shown in FIG. 10, the X-ray detector 15 includes a first detection unit 16a which is disposed on the optical axis O of the X-ray optical member 30, a second detection unit 16b which surrounds the surroundings of the first detection unit 16a, and a third detection unit 16c which surrounds the surroundings of the second detection unit 16b. The third detection unit 16c is constituted of a plurality of TESs (for example, 12 TESs) segmented in the surroundings of the second detection unit 16b. The third detection unit 16c is constituted of a TES, in which counting efficiency is further given priority over energy resolution, in contrast to the second detection unit 16b.

In the X-ray analysis device 10 of the above-described embodiment, although the surrounding shield 20 is formed in a shape extending so as to cover the cold head 18, thereby constituting a part of the snout 17b, the invention is not limited thereto.

Figure 11:
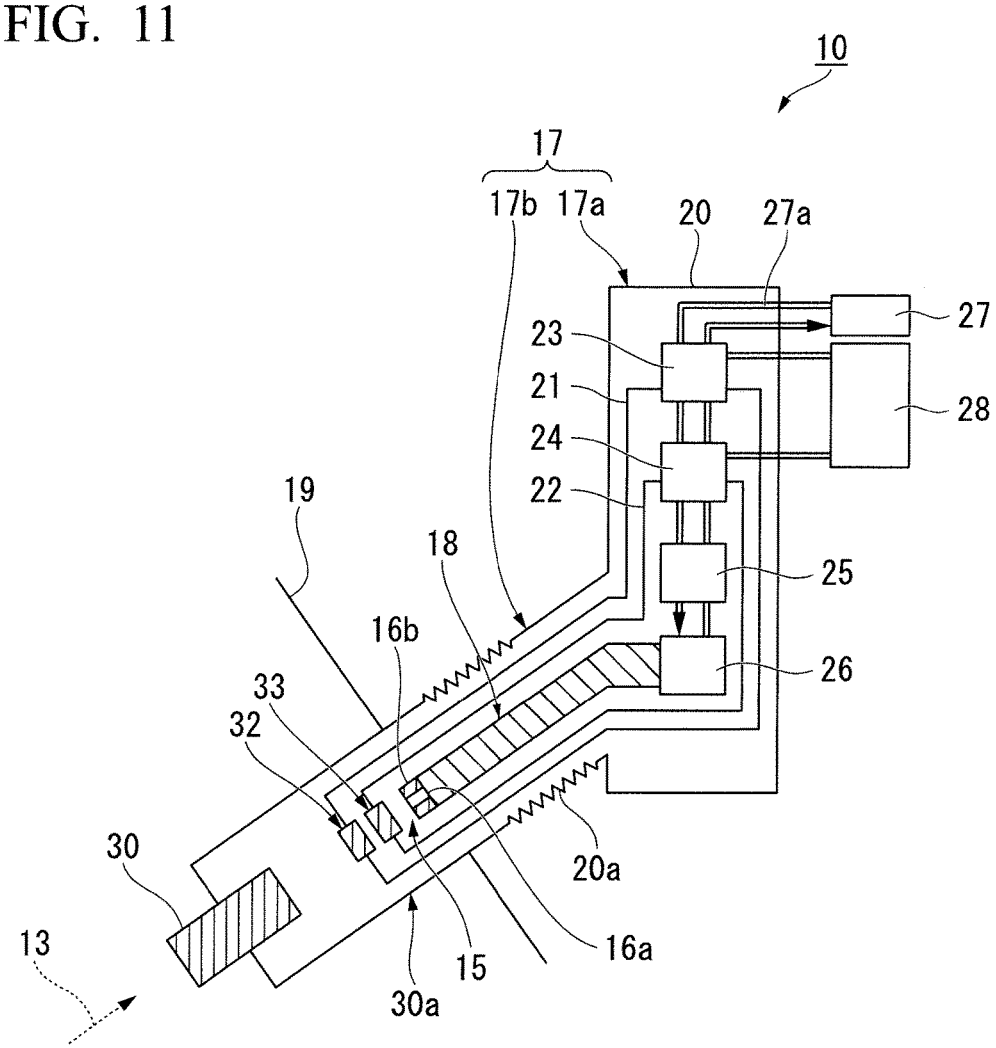
FIG. 11 is a sectional view schematically showing the configuration of a cooling unit in an X-ray analysis device according to a fifth modification example of the embodiment of the invention, and is a diagram showing a configuration in which an X-ray optical member fixing portion and a tubular portion are incorporated as a part of a snout.

In a fifth modification example of the embodiment, as shown in FIG. 11, the extension portion of the surrounding shield 20 may constitute the bellows tubular portion 20a, and the surrounding X-ray window 31 may be omitted. In the fifth modification example, a part of each of the first heat shield 21 and the second heat shield 22 is formed in a shape extending so as to cover the cold head 18, thereby constituting the snout 17b.

In the X-ray analysis device 10 of the above-described embodiment, although the first detection unit 16a is disposed such that the surroundings thereof is surrounded by the second detection unit 16b, the invention is not limited thereto.

In a sixth modification example of the embodiment, as shown in FIG. 12, the second detection unit 16b may be disposed such that the surroundings thereof is surrounded by the first detection unit 16a. The second detection unit 16b is constituted of, for example, a single TES disposed in a central portion. The first detection unit 16a is constituted of a plurality of TESs (for example, 12 TESs) segmented in the surroundings of the second detection unit 16b.

In the sixth modification example, in a case where the distance between the second detection unit 16b and the X-ray optical member 30 substantially coincides with the focal distance of the X-ray optical member 30, it is possible to appropriately perform analysis, such as fast analysis, in which counting efficiency is given priority.

Hereinafter, other modification examples will be described.

In the X-ray analysis device 10 of the above-described embodiment, although each of the first detection unit 16a and the second detection unit 16b of the X-ray detector 15 are formed of a superconducting transition edge sensor (TES), the invention is not limited thereto.

An X-ray detector 15 of an X-ray analysis device 10 according to a modification example of the above-described embodiment may be constituted of, for example, other energy dispersive X-ray detectors, such as a silicon drift type detector, an STJ, an SSPD, an SSLD, and an MKID.

The X-ray detector 15 may be constituted of, for example, an appropriate combination of a plurality of energy dispersive X-ray detectors having different detection characteristic, such as silicon drift type detector, a TES, an STJ, an SSPD, an SSLD, and an MKID. The X-ray detector 15 may be configured such that, for example, the first detection unit 16a in which energy resolution is given priority is formed of a TES, and the second detection unit 16*b* in which counting efficiency is given priority is formed of a silicon drift type detector, an STJ, or the like.

In the above-described embodiment, although the X-ray analysis device 10 includes the two X-ray windows including the first X-ray window 32 and the second X-ray window 33, the invention is not limited thereto.

In an X-ray analysis device 10 according to a modification example of the above-described embodiment, the first X-ray window 32 in the X-ray analysis device 10 of the above-described embodiment may be omitted. In this modification example, the first heat shield 21, the first pot 23, and the first X-ray window 32 may be omitted.

According to this modification example, if the cooling output of the second pot 24 is sufficient to such an extent that the temperature T2 of the second X-ray window 33 can be maintained at 1 K to 5 K, it is possible to simplify the device configuration of the X-ray analysis device 10 while thermally stably operating the TESs of the first detection unit 16*a* and the second detection unit 16*b*.

In the above-described embodiment, although the X-ray analysis device 10 includes the two X-ray windows including the first X-ray window 32 and the second X-ray window 33, the invention is not limited thereto. A larger number (for example, three or the like) of X-ray windows than two may be provided.

According to this modification example, it is possible to prevent an increase in temperature of the TES due to heat radiation by lowering the temperature in a stepwise manner using multiple X-ray windows from an atmosphere temperature around the sample 11 to be analyzed toward the TESs of the first detection unit 16*a* and the second detection unit 16*b*, and to more stably secure desired operation characteristics.

In the above-described embodiment, the X-ray analysis device 10 may include a collimator which is fixed to the TES, the cold head 18, a pedestal (not shown), or the like. An X-ray window may be provided in the collimator.

In the above-described embodiment, the refrigerator body 17*a* and the pre-cooler 28 may be, for example, a mechanical refrigerator, such as a Stirling refrigerator or a pulse tube refrigerator, or a refrigerator using a refrigerant, such as liquid helium or decompressed 3He.

The technical scope of the invention is not limited to the above-described embodiment, and is provided with a configuration in which various changes are made on the above-described embodiment without departing from the gist of the invention. That is, the configuration of the above-described embodiment is a mere example, and can be appropriately changed.

EXPLANATION OF REFERENCES

11: sample, 12: electron beam, 13: characteristic X-rays, 14: electron gun, 15: X-ray detector, 16*a*: first detection unit, 16*b*: second detection unit, 17: cooling unit, 17*a*: refrigerator body, 17*b*: snout, 18: cold head, 19: chamber, 20: surrounding shield, 21: first heat shield, 22: second heat shield, 23: first pot, 24: second pot, 25: still, 26: mixer (mixing chamber), 27: gas circulator, 27*a*: gas circulation flow passage, 28: pre-cooler, 30: X-ray optical member, 30*a*: X-ray optical member fixing portion, 31: surrounding X-ray window, 32: first X-ray window, 33: second X-ray window, 41: processing unit, 42: distance changing mechanism, 43: drive unit, 44: control unit, 51: sensor circuit unit, 52: bias current source, 53: current detection mechanism, 54: thermometer, 72: distance changing mechanism

What is claimed is:

1. An X-ray analysis device comprising:
an excitation source which excites a sample to be analyzed to emit characteristic X-rays;
a plurality of detection units which detect the characteristic X-rays emitted from the sample;
an optical member which guides the characteristic X-rays emitted from the sample to at least any one of the plurality of detection units; and
a distance changing mechanism which changes a distance between each of the plurality of detection units and the optical member in an axial direction of an optical axis of the optical member,
wherein the plurality of detection units include at least a first detection unit and a second detection unit having different detection characteristics,
the first detection unit is formed such that energy resolution is given relative priority over counting efficiency in contrast to the second detection unit, and
the second detection unit is formed such that counting efficiency is given relative priority over energy resolution in contrast to the first detection unit.

2. The X-ray analysis device according to claim 1, wherein either one of the first detection unit and the second detection unit is disposed at a position relatively close to the optical axis, and the other of the first detection unit and the second detection unit is disposed at a position relatively distant from the optical axis.

3. The X-ray analysis device according to claim 2, wherein the second detection unit is disposed so that surroundings of the first detection unit are surrounded.

4. The X-ray analysis device according to claim 1, wherein the distance changing mechanism realizes
a first state where the distance is set to a first distance such that an irradiation region of the characteristic X-rays guided by the optical member is included in an effective detection region of the first detection unit, and
a second state where the distance is set to a second distance such that the irradiation region of the characteristic X-rays guided by the optical member is included in an effective detection region of the second detection unit.

5. The X-ray analysis device according to claim 1, further comprising:
a dead time acquisition unit which acquires a dead time for the detection of the characteristic X-rays in the plurality of detection units,
wherein the distance changing mechanism changes the distance so as to maintain the dead time to be less than a predetermined threshold.

6. The X-ray analysis device according to claim 1, further comprising:
a frequency acquisition unit which acquires an overlap frequency of detection signals of the characteristic X-rays in the plurality of detection units,
wherein the distance changing mechanism changes the distance so as to maintain the overlap frequency of the detection signals to be less than a predetermined threshold.

* * * * *